US00PP22912P2

(12) United States Plant Patent
Danziger

(10) Patent No.: US PP22,912 P2
(45) Date of Patent: Jul. 31, 2012

(54) ***ANGELONIA* PLANT NAMED 'DALON9'**

(50) Latin Name: *Angelonia angustifolia*
Varietal Denomination: DALON9

(75) Inventor: Gavriel Danziger, Moshav Mishmar Hashiva (IL)

(73) Assignee: Danziger 'DAN' Flower Farm, Beit Dagan (IL)

( * ) Notice: Subject to any disclaimer, the term of this patent is extended or adjusted under 35 U.S.C. 154(b) by 0 days.

(21) Appl. No.: 13/066,745

(22) Filed: Apr. 22, 2011

(51) Int. Cl.
*A01H 5/00* (2006.01)

(52) U.S. Cl. ..... Plt./404

(58) Field of Classification Search ..... Plt./404
See application file for complete search history.

*Primary Examiner* — Annette Para

(74) *Attorney, Agent, or Firm* — Cassandra Bright

(57) ABSTRACT

A new and distinct *Angelonia* cultivar named 'DALON9' is disclosed, characterized by large blue flowers and a compact plant habit. The new variety is an *Angelonia*, normally produced as an outdoor garden or container plant.

2 Drawing Sheets

Latin name of the genus and species: *Angelonia angustifolia.*

Variety denomination: 'DALON9'.

BACKGROUND OF THE INVENTION

The new *Angelonia* cultivar is a product of a planned breeding program conducted by the inventor, Gavriel Danziger, in Moshav Mishmar Hashiva, Israel. The objective of the breeding program was to produce new *Angelonia* varieties for ornamental commercial applications. The cross resulting in this new variety was made during December 2008.

The seed parent is the unpatented, proprietary seedling variety referred to as *Angelonia angustifolia* 'CV504' The pollen parent is the unpatented proprietary seedling variety referred to as *Angelonia angustifolia* 'CV444'. The new variety was discovered in April 2009 by the inventor in a group of seedlings resulting from the 2008 crossing, in a research greenhouse in Moshav Mishmar Hashiva, Israel.

Asexual reproduction of the new cultivar 'DALON9' by vegetative cuttings was first performed at a research greenhouse in Moshav Mishmar Hashiva, Israel in April 2009 and has shown that the unique features of this cultivar are stable and reproduced true to type in successive generations.

SUMMARY OF THE INVENTION

The cultivar 'DALON9' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DALON9' These characteristics in combination distinguish 'DALON9' as a new and distinct *Angelonia* cultivar:

1. Compact growth habit
2. Large flower size

Plants of the new cultivar 'DALON9' are similar to plants of the seed parent, *Angelonia angustifolia* 'CV504' in most horticultural characteristics, however, plants of the new cultivar 'DALON9' have a more compact plant habit, and larger flowers.

Plants of the new cultivar 'DALON9' are similar to plants of the pollen parent, *Angelonia angustifolia* 'CV444' in most horticultural characteristics, however, plants of the new cultivar 'DALON9' produce dark blue flowers, compared to pink flowers found on the pollen parent. Additionally, the new variety produces larger flowers than the pollen parent.

COMMERCIAL COMPARISON

Plants of the new cultivar 'DALON9' are comparable to the variety *Angelonia* 'DANGELONI3' U.S. Plant Pat. No. 19,456. The two *Angelonia* varieties are similar in most horticultural characteristics however, the new variety 'DALON9' differs in having different color flowers, and larger flowers.

BRIEF DESCRIPTION OF THE PHOTOGRAPHS

Figure 1:
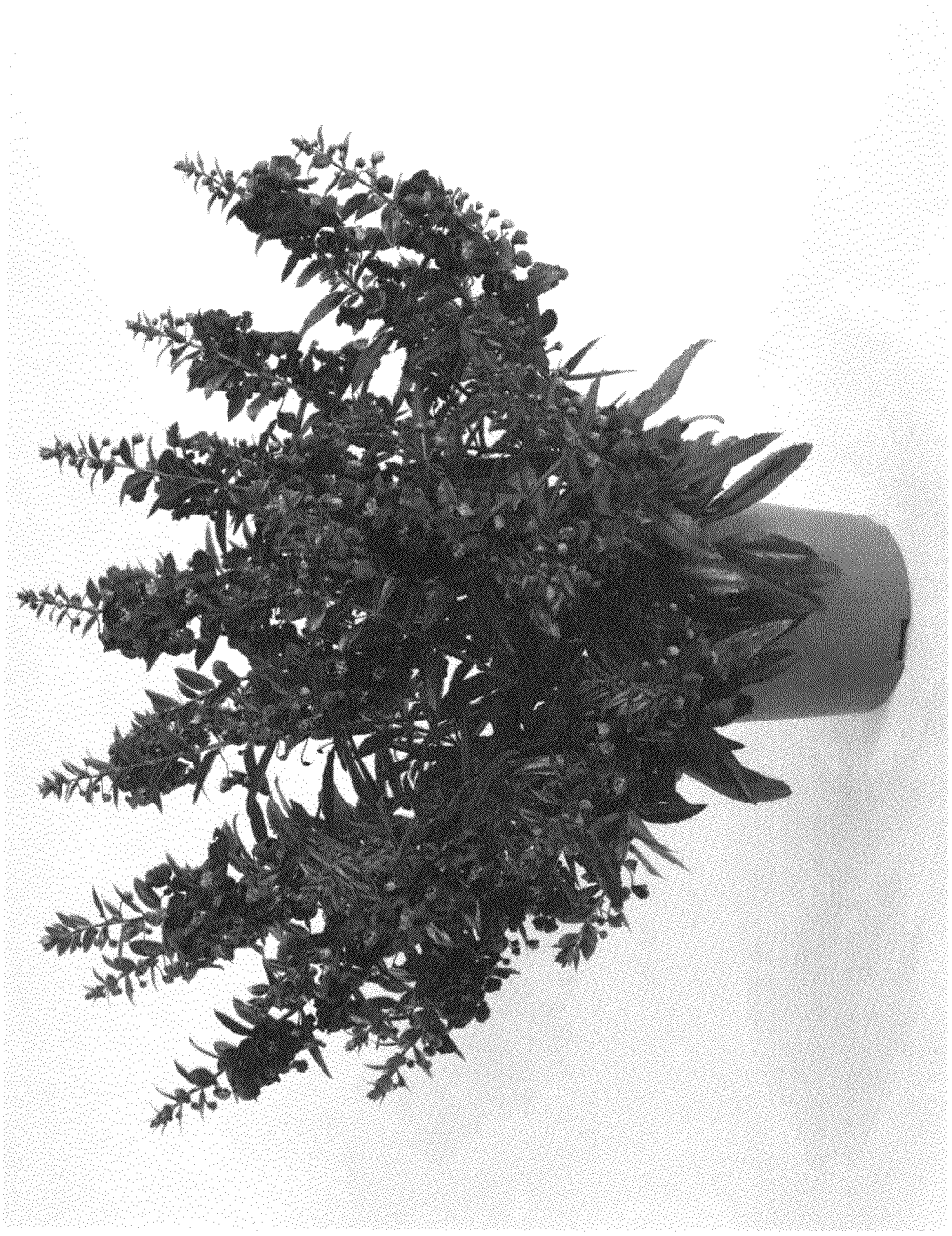

The accompanying photograph in FIG. 1 illustrates in full color a typical plant of 'DALON9' grown in a greenhouse, in a 13 cm pot. Age of the plant photographed is approximately 9 weeks from a rooted cutting.

Figure 2:
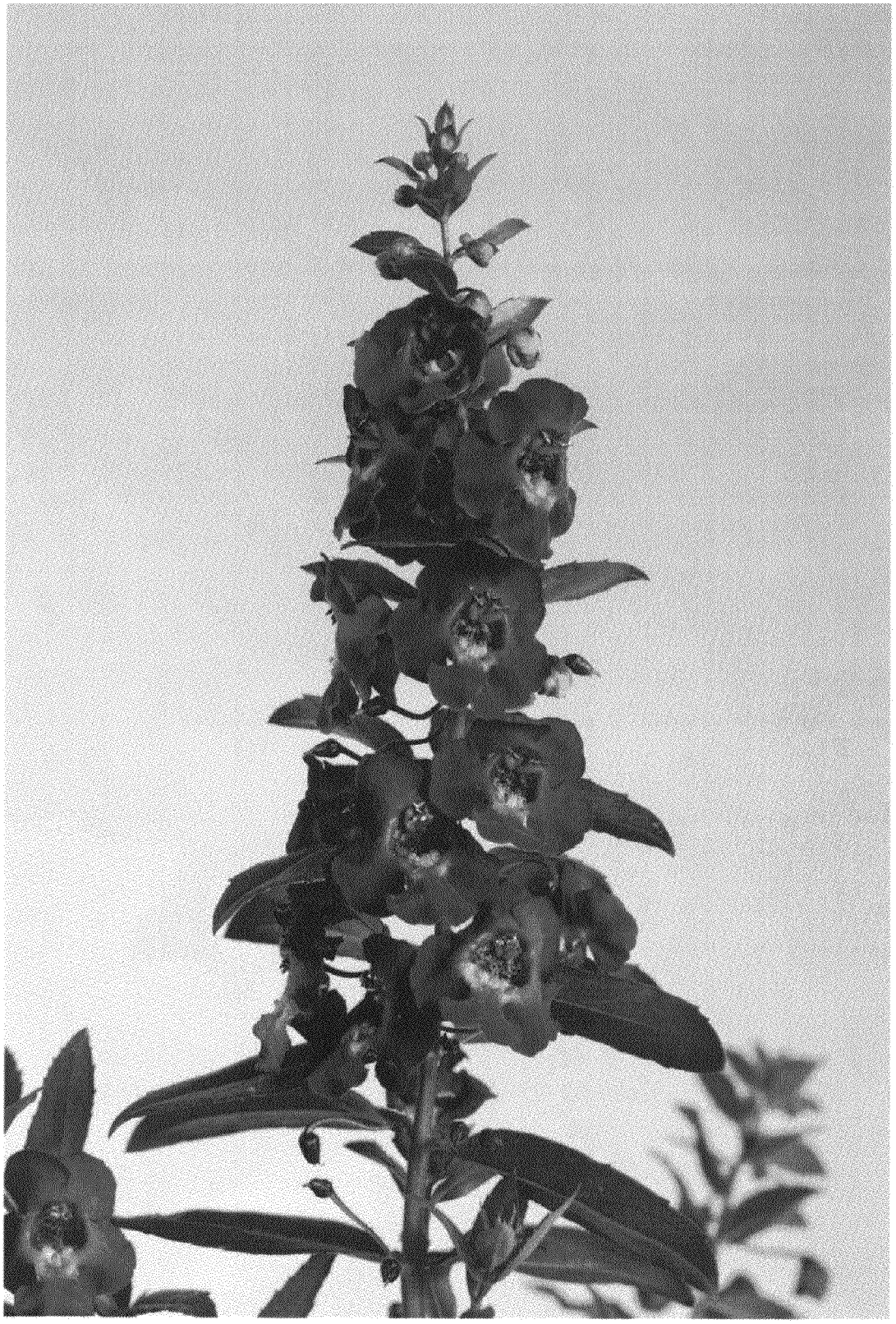

FIG. 2 illustrates in full color a close up of a typical bloom of 'DALON9'. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001 except where general terms of ordinary dictionary significance are used. The following observations and measurements describe 'DALON9' plants grown outdoors during Spring in Moshav Mishmar Hashiva, Israel. The growing temperature ranged from 15° C. to 30° C. during the day and from 12° C. to 20° C. during the night. General light conditions are bright, normal sunlight. Measurements and numerical values represent averages of typical plant types.

Botanical classification: *Angelonia angustifolia* 'DALON9'.

PROPAGATION

Time to initiate roots: About 10 to 15 days at approximately 22° C.

Root description: Fine, fibrous, very well branched.

PLANT

Growth habit: Upright annual.

Pot size of plant described: 13 cm.

Height: To top of foliage: Approximately 30 cm. To top of flowers: Approximately 30 cm.

Plant spread: Approximately 30 cm.

Growth rate: Rapid.

Branching characteristics: Moderate.

Length of primary lateral branches: Approximately 30 cm.

Diameter of lateral branches: Approximately 0.5 cm.

Quantity of primary lateral branches: Average 15.

Characteristics of primary lateral branches:

*Form*.—Round.

*Diameter*.—0.5 cm.

*Color*.—Near RHS Green 137A.

*Texture*.—Smooth.

*Strength*.—Moderate, prone to breakage.

Internode length: Approximately 1 to 1.5 cm.

FOLIAGE

Leaf:

*Arrangement*.—Opposite.

*Quantity*.—Approximately 20 per branch.

*Average length*.—Range between 4-15 cm.

*Average width*.—2 cm.

*Shape of blade*.—Lanceolate.

*Apex*.—Rounded.

*Base*.—Acute.

*Margin*.—Scalloped.

*Texture of top surface*.—Smooth.

*Pubescence*.—No.

*Angle of attachment*.—50°.

*Aspect*.—Flat.

*Color*.—Young foliage upper side: RHS Green 137 A. Young foliage under side: RHS Green 137 A. Mature foliage upper side: RHS Green 137 A. Mature foliage under side: RHS Green 137 A.

*Venation*.—Type: Pinnate. Venation color upper side: RHS Green 137 A. Venation color under side: RHS Green 137 A.

*Petiole*.—Not present.

FLOWER

Natural flowering season: Spring & summer.

Days to flowering from rooted cutting: 60.

Inflorescence and flower type and habit: Panicle.

Rate of flower opening: 4 to 14 days from bud to fully opened flower.

Flower longevity on plant: 5 days.

Persistent or self-cleaning: Self-Cleaning.

Bud:

*Shape*.—Sphere.

*Length*.—Approximately 0.5 cm.

*Diameter*.—Approximately 0.5 cm.

*Color*.—Near RHS Yellow-Green 145B.

Flower size:

*Diameter*.—About 3.0 cm.

*Length*.—About 2.0 cm.

Corolla/petals:

*Petals*.—Length: 1 cm. Diameter: 1.3 cm. Quantity: 7. Texture: Smooth. Apex: Rounded.

*Color*.—When opening: Upper surface: Near RHS Violet N83A. Lower surface: Near RHS Violet N83A. Fully opened: Upper surface: Near RHS Violet N83A. Lower surface: Near RHS Violet N83A.

Sepals:

*Quantity per flower*.—5.

*Shape*.—Rounded.

*Length*.—0.4 cm.

*Width*.—0.2 cm.

*Apex*.—Blunt.

*Base*.—Obtuse.

*Margin*.—Entire.

*Texture*.—Smooth.

*Color*.—Near RHS 137A Green.

Peduncle:

*Length*.—1-2 cm.

*Color*.—Near RHS Green 137A with flush Violet 83A.

*Strength*.—Medium.

*Angle*.—50°.

Pedicel:

*Length*.—2 cm.

*Diameter*.—0.1 cm.

*Color*.—Near RHS Greyed-Purple N186C.

Fragrance: No.

REPRODUCTIVE ORGANS

Stamens:

*Number*.—2.

*Filament length*.—1 mm.

Anthers:

*Shape*.—Conical.

*Length*.—0.2 cm.

*Color*.—Near RHS Violet N88A.

Pollen:

*Color*.—Near RHS Green-Yellow 1D.

*Quantity*.—Moderate to scant.

Pistil:

*Number*.—2.

*Length*.—0.1 cm.

*Style*.—Length: 0.1 cm. Color Near RHS White 155D.

*Stigma*.—Shape: Acute deltoid. Color: Near RHS White 155D.

OTHER CHARACTERISTICS

Seeds and fruits: Seeds and fruits: Not observed to date.

Disease/pest resistance: Neither resistance nor susceptibility to pathogens and pests common to *Angelonia* have been observed.

Temperature tolerance: The new variety tolerates temperatures between 5 to 42° C.

What is claimed is:

1. A new and distinct cultivar of *Angelonia* plant named 'DALON9' as herein illustrated and described.

* * * * *